(12) United States Patent
Wang

(10) Patent No.: US 7,197,169 B2
(45) Date of Patent: Mar. 27, 2007

(54) METHOD FOR DETECTING A RESPONSE OF EACH PROBE ZONE ON A TEST STRIP

(76) Inventor: Kuo-Jeng Wang, 14, Kung-An St, Ksiao-Kang, Kaohsiung City (TW)

( * ) Notice: Subject to any disclaimer, the term of this patent is extended or adjusted under 35 U.S.C. 154(b) by 768 days.

(21) Appl. No.: 10/334,798

(22) Filed: Jan. 2, 2003

(65) Prior Publication Data

US 2004/0131238 A1   Jul. 8, 2004

(51) Int. Cl.
   *G06K 9/00*   (2006.01)
   *G01N 21/00*   (2006.01)
   *C12Q 1/00*   (2006.01)
(52) U.S. Cl. .................. 382/128; 382/168; 422/56; 422/82.05; 435/4; 435/805
(58) Field of Classification Search .............. 382/101, 382/102, 128, 129, 164, 168, 174, 183, 169–172; 358/449, 464; 435/805, 4; 422/82.05, 56
See application file for complete search history.

(56) References Cited

U.S. PATENT DOCUMENTS

| | | | | |
|---|---|---|---|---|
| 3,745,527 A | * | 7/1973 | Yoshimura et al. | 382/135 |
| 5,323,473 A | * | 6/1994 | Lau | 382/175 |
| 5,408,535 A | * | 4/1995 | Howard et al. | 382/128 |
| 5,969,371 A | * | 10/1999 | Andersen et al. | 250/559.15 |
| 6,689,618 B1 | * | 2/2004 | Chen | 436/135 |
| 2001/0034068 A1 | * | 10/2001 | Spivey et al. | 436/518 |
| 2002/0081233 A1 | * | 6/2002 | Lappe et al. | 422/82.05 |
| 2003/0040128 A1 | * | 2/2003 | Meador et al. | 436/518 |

* cited by examiner

*Primary Examiner*—Andrew W. Johns
*Assistant Examiner*—Anthony Mackowey
(74) *Attorney, Agent, or Firm*—Berkeley Law & Technology Group, LLP

(57) ABSTRACT

A method for detecting a response (grey level) of each probe zone on a test strip includes providing a test strip having a color pattern. The color pattern occurs in response to a solution contacting with the test strip and includes color lines arranged in sequence. Each color line represents a probe zone of the test strip. A whole image of the test strip is captured and is selected at least one scan line perpendicular to the color lines. A pixel position of the scan line having a minimum pixel value corresponding to a bottom edge of the test strip is set and the pixel position is used as a reference to identify respective pixel positions of the color lines on the scan line.

27 Claims, 3 Drawing Sheets

METHOD FOR DETECTING A RESPONSE OF EACH PROBE ZONE ON A TEST STRIP

BACKGROUND OF THE INVENTION

1. Field of the Invention

The present invention relates to a method for detecting a response of each probe zone on a test strip, and more particularly to a method for detecting a response of each probe zone on a test strip via an image capturing technology.

2. Description of the Prior Art

Over the past decade, there has been an increased need and demand for analysis of various biological specimens, for purposes ranging from pregnancy testing to drug analysis. Considerable time and effort has been expended by way of devising systems and analytic techniques to ensure reliable testing and accurate results.

Moreover, with increasing rise in the use of abuse-type drugs, the need for detecting and identifying those drugs and their metabolites is becoming more important. With this need, many more tests are required to monitor the use of abuse-type drugs.

Thin layer chromatography (TLC) screening procedures for detecting drugs in urine require the careful preparation of a test specimen and then a skillful application of that test specimen to a plate placed into a developing chamber. Once the plate is removed from the chamber and dried, it is sprayed with visualization reagents. Location and color of spots are compared with those of known standards. Qualitative judgements are made as to the presence of various drugs in the unknown sample. The procedure is tedious, time consuming and requires skilled personnel to interpret the results.

The EMIT (Enzyme Multiplied Immuno-chemical Test) procedure is a semi-quantitative immuno-assay for drugs of abuse in biological fluids. The laboratory test requires trained technicians to perform and the equipment necessarily costs several thousands of dollars.

The RIA (Radio-Immuno-Assay) procedure is a sensitive and quantitative laboratory procedure for detecting drugs of abuse. The various immunochemicals are labeled with radioactive compounds and require special care in their use and disposal. A license is required from the government to use this laboratory procedure because of the presence of radioactive materials. The GLC (Gas-Liquid Chromatography) procedure can provide the highest degree of accuracy in drug analysis. However, the necessary equipment is expensive and the procedure is complicated. Consequently, highly trained personnel are required for its use.

Each of these well-known procedures requires skilled technicians and relatively sophisticated equipment. Consequently, the testing procedure is necessarily expensive.

However, the increase of drug abuse has increased a need for new methods of analyzing drug residues in physiological fluid. A drug abuse test paper for testing the presence or absence of drugs in a fluid specimen collected from a test subject is developed. The drug abuse test paper is prepared in accordance with unique procedure whereby pH insensitivity and color change sensitivities to tested fluids are obtained. The color change of the drug abuse test paper sensitive to one specific substance present in the fluid specimen collected from the test subject applied on the drug abuse test paper is simply verified by visual judgement. This abuse-type drug testing is rapid and convenient. However, it is not convincing for concluding the test subject has used abuse-type drugs.

Accordingly, it is an intention to provide means capable of detecting and identifying the presence or absence of drugs of abuse in a fluid specimen, which can overcome the problems of the conventional methods.

SUMMARY OF THE INVENTION

It is one objective of the present invention to provide a method for detecting a response of each probe zone on a test strip, which captures a whole image of the test strip and using the image position of a bottom edge of the test strip as a reference to identify the image positions of the responses of the probe zones of the test strip. The responses of the probe zones of the test strip thus can be accurately and rapidly determined in accordance with the gray levels of the related image positions.

It is another objective of the present invention to provide a method for detecting a response of each probe zone on a test strip, which can be used as an implement to detect or identify the presence or absence of drugs of abuse in a test sample.

It is still another objective of the present invention to provide a method for detecting a response of each probe zone on a test strip, which is quick and convenient to use by non-sophisticated personnel in non-laboratory settings, and performs assays for multiple drugs of abuse simultaneously.

It is a further objective of the present invention to provide a method for detecting a response of each probe zone on a test strip, which associates with an image capturing/processing technology to analyze drug residues in physiological fluid to attain the purposes of accuracy, rapid and cost effective in drug abuse detection technology.

In order to achieve the above objectives of this invention, the present invention provides a method for detecting a response for each probe zone on a test strip. The present method includes providing a test strip having a light color base and a color pattern displayed thereon. The color pattern occurs in response to a tested solution contacting with the test strip and including a plurality of color lines displayed in sequence from a bottom portion of the test strip to a top portion thereof. The site of each color line represents a probe zone of the test strip. Capturing a whole image of the test strip and selecting at least one scan line perpendicular to the image of the color lines from the whole image. Setting a pixel position of the scan line having a minimum pixel value corresponding to the image of a bottom edge of the test strip. And, assigning respective pixel positions of the scan line corresponding to each of the color lines of the test strip by using the pixel position with the minimum pixel value as a reference and in accordance with the sequence of the color lines displayed on the test strip. Thereby, a response of each probe zone of the test strip related to a respective pixel value of the pixel position corresponding to the color line of the probe zone is obtained.

BRIEF DESCRIPTION OF THE DRAWINGS

The objectives and features of the present invention as well as advantages thereof will become apparent from the following detailed description, considered in conjunction with the accompanying drawings.

DESCRIPTION OF THE PREFERRED EMBODIMENT

From a view of broad application, the present invention provides a method for detecting a response for each probe zone on a test strip after testing a sample solution, which associates with an image capturing/processing technology to detect respective responses of the probe zones on the test strip to qualitatively and quantitatively identify specific substances in the sample solution. More specifically, the present invention utilizes the image capturing technology to capture the whole image of a test strip having a color pattern displayed thereon. The color pattern includes a plurality of color lines each of which representing a probe zone of the test strip having a color change in response to a specific substance in the sample solution. In accordance with the image of the color pattern of the test strip, the response of each probe zone of the test strip to the sample solution can be determined so as to detect the presence or absence of the specific substance related to in the sample solution. The present method is suitable to be used as a drug abuse detection technology. That is, the present method can be used to detect the response for each probe zone on a drug abuse test strip after testing a physiological fluid, such as a urine specimen fluid, collected from a test subject, instead of visual judgment of the responses of the probe zones on the drug abuse test strip.

Figure 1A:
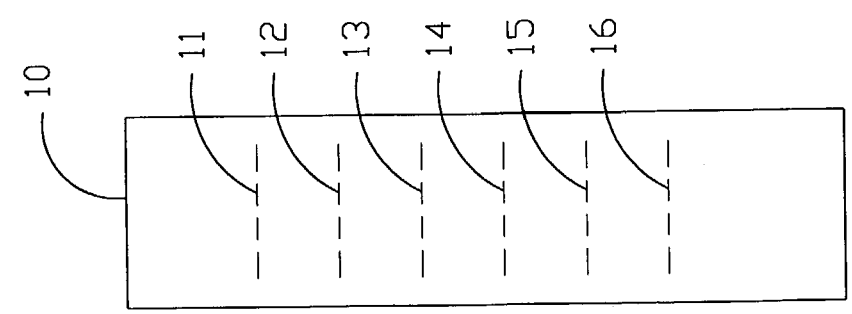
FIG. 1A to FIG. 1D shows schematic top views of a drug abuse test strip under various testing situations of the present invention.

The present method will be described in detail with a drug abuse test strip as an example in the following. However, before detailed description of the present method, an introduction of various color patterns occurring on one drug abuse test strip under various testing situations is provided herein. Firstly, referring to FIG. 1A, which is a schematic top view of a drug abuse test strip 10 prior to testing a sample fluid collected from a test subject. The drug abuse test strip 10 is blank and no color pattern displayed thereon prior to testing the sample fluid. The dotted lines 11 through 16 respectively represent a probe zone of the drug abuse test strip 10. The top probe zone of the drug abuse test strip 10 corresponding to the site of dotted line 11 displays color change in response to the sample fluid, which is used to indicate whether the amount of the sample fluid is sufficient to move through all probe zones of the drug abuse test strip 10 by capillary action. The other probe zones of the drug abuse test strip 10 corresponding to the sites of dotted lines 12 through 16 respectively display color change in response to a respective abuse-type drug presenting in the sample fluid. It should be noted the drug abuse test strip used in the present invention is not limited to the kind of the drug abuse test strip 10 of FIG. 1A.

Figure 1B:
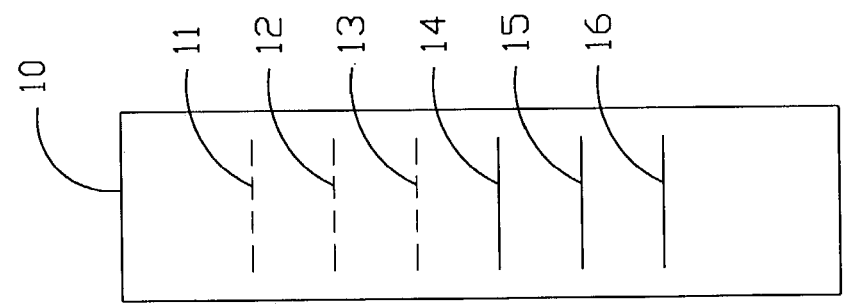
Figure 1C:
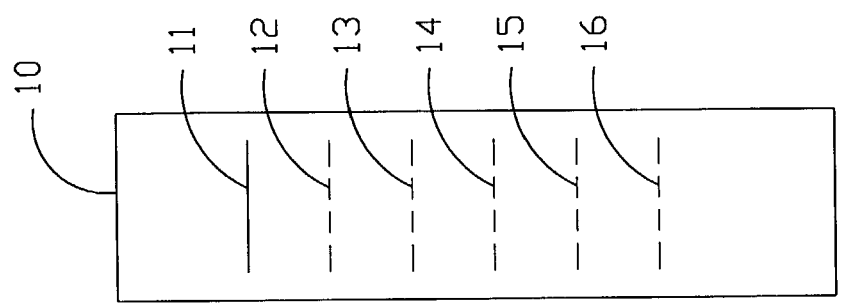
Figure 1D:
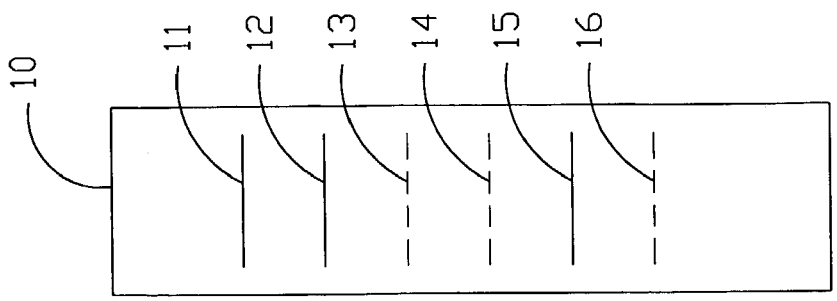

FIG. 1B shows a color pattern of the drug abuse test strip 10 having no color change occurring in the top probe zone represented by the dotted line 11, which is under a testing situation where the amount of the sample fluid is not sufficient to assure the sample fluid moves through all probe zones of the drug abuse test strip 10. Therefore, in accordance with the color pattern consisting of solid lines 14 through 16 shown in FIG. 1B, the drugs of abuse present in the sample fluid cannot completely detected and identified. FIG. 1C shows a color pattern of the drug abuse test strip 10 having only one color line 11 displayed in the top probe zone of the drug abuse test strip 10. This means all other probe zones represented by the dotted lines 12 through 16 have positive responses to the sample fluid, and all drugs of abuse corresponding to these probe zones are present in the sample fluid. FIG. 1D shows a color pattern of the drug abuse test strip having color lines 11, 12 and 15 displayed in the top probe zone and some other probe zones of the drug abuse test strip 10. This means the top probe zone 11 has a positive response to the sample fluid, indicating the amount of the sample fluid is sufficient, and the probe zones represented by the color lines 12 and 15 have a negative response to the sample fluid, indicating that the absence of the drugs of abuse corresponding to these two probe zones in the sample fluid. On the contrary, the probe zones represented by the dotted lines 13, 14 and 16 have a positive response to the sample fluid, indicating the presence of the drugs of abuse corresponding to these three probe zones in the sample fluid.

The present invention associates with image capturing/processing technology to detect responses for the respective probe zones of the drug abuse test strip 10. The color pattern including various color lines displayed on the drug abuse test strip 10 after testing the sample fluid is captured and analyzed to identify the drugs of abuse present in the sample fluid. FIGS. 1B to 1D depict some testing situations. One first testing situation is the color line 11 is not displayed due to an insufficient amount of the sample fluid, see FIG. 1B. A second testing situation is only the color line 11 displayed, while other color lines 12 through 16 are not, which indicates that all the probe zones of the drug abuse test strip 10 have a positive response to the sample fluid. Thus, all the drugs of abuse corresponding to all the probe zones are present in the sample fluid, as shown in FIG. 1C. A third testing situation is the color line 11 and some other color lines 12 and 15 are displayed, which indicates the probe zones of the color lines 12 and 15 have a negative response to the sample fluid. The drugs of abuse related to these lines are absent in the sample fluid. In view of the test results under the various testing situations, the image information of the respective color lines 12 through 16 can not be identified with the color line 11 as a reference.

Figure 2A:
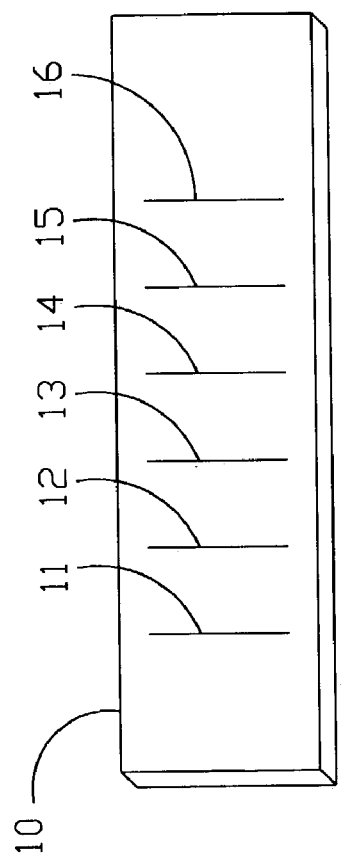
FIG. 2A is a schematic perspective view of a drug abuse test strip after testing a sample fluid of the present invention.

Hence, the present invention provides a method to identify the image information of the respective color lines 11 through 16 of the drug abuse test strip 10 under the various testing situations. Referring to FIG. 2A, the drug abuse test strip 10 having a light color base, such as white base, and a color pattern displayed thereon, is provided. The color pattern includes color lines 11 through 16 displayed in sequence from the top portion of the drug abuse test strip 10 to the bottom portion thereof. The color lines 11 through 16 have the same color, while different shades. The site of each of the color lines 11 through 16 represents a probe zone of the drug abuse test strip 10. Except for the top probe zone represented by the color line 11, if the probe zone has a positive response to the sample fluid, the site of the probe zone would display a light shade color line, even if it does not display the color line. That indicates the presence of the drug of abuse to be detected present in the sample fluid. On the contrary, when the probe zone has a negative response to the sample fluid, the site of the probe zone would display a dark shade color line, indicating the absence of the drug of abuse to be detected in the sample fluid. In the present invention, the shade of the color line is inversely proportional to the concentration of the detected drug of abuse in the sample fluid. The whole image of the drug abuse test strip 10 is then captured by an image capturing device, such as a scanner associated with a charge-coupled device (CCD).

Figure 2B:
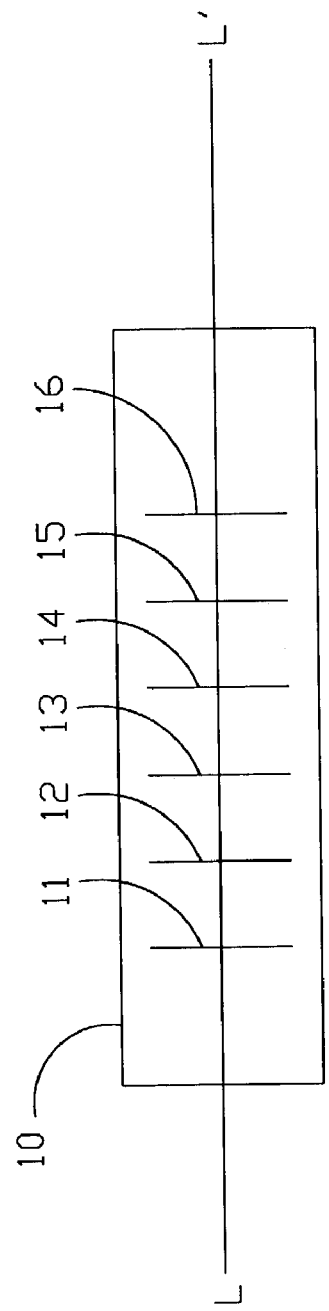
FIG. 2B is a schematic top view of the drug abuse test strip of FIG. 2A.
Figure 3:
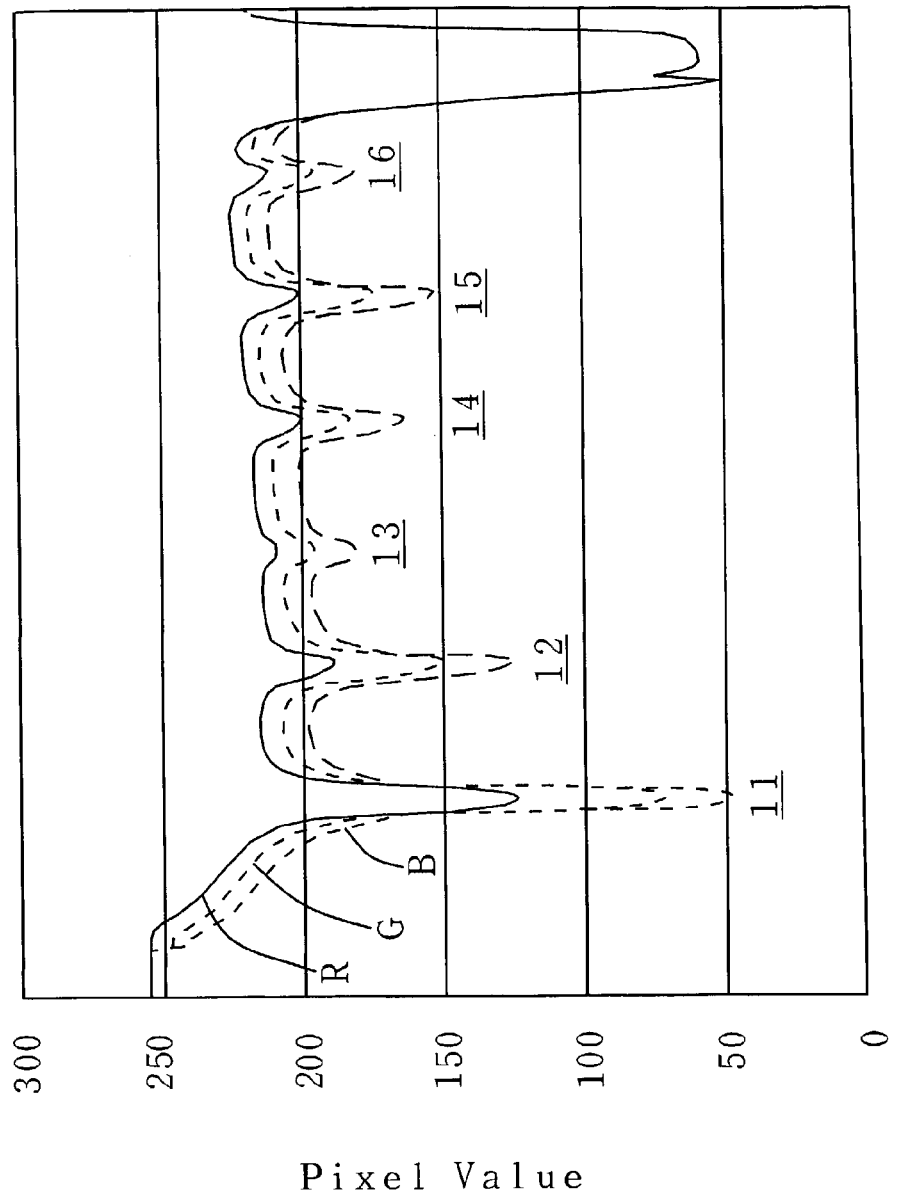
FIG. 3 is a diagram of pixel value verse pixel position established in accordance with one scan line selected from a whole image captured from the drug abuse test strip of FIG. 2B.

FIG. 2B shows selecting at least one scan line L—L from the whole image. The scan line L—L is perpendicular to the image of the color lines 11 through 16. A diagram of pixel value verse pixel position for the whole image of the drug abuse test strip 10 is established in accordance with the scan line L—L, as shown in FIG. 3. The diagram of FIG. 3 shows three curves respectively representing the relationship of pixel value and pixel position for red (R), green (G), blue (B) channels of the charge-coupled device. The R,G,B channels are disposed on the charge-coupled device in parallel, and each of the R,G,B channels includes a plurality of sensor cells, and each sensor cell corresponds to a pixel position. Alternately, the present invention can utilize a charge-coupled device with a single channel, such as a charge-coupled device with a red channel, a charge-coupled device with a green channel or a charge-coupled device with a blue channel, to capture the whole image of the drug abuse test strip 10. A shade would appear on the bottom edge of the drug abuse test strip 10 due to the three-dimensional structure of the drug abuse test strip 10. The shade of the bottom edge of the drug abuse test strip 10 would correspond to an image position having a minimum gray level, i.e. minimum pixel value, on the whole image of the drug abuse test strip 10. Thus, referring to FIG. 3, setting a pixel position of the scan line L—L having a minimum pixel value, the position between pixel positions 301 and 326, corresponds to the image of the bottom edge of the drug abuse test strip 10. As shown in FIG. 3, the R pixel values of the whole image of the drug abuse test strip 10 show significant differences. It is preferable that the pixel position corresponding to the bottom edge of the drug abuse test strip 10 is determined depending on the minimum R pixel value. Then, using the pixel position having the minimum pixel value as a reference, i.e. designating the position between pixel positions 301 and 326 corresponding to the bottom edge of the drug abuse test strip 10, and in accordance with the sequence of the color lines 11 through 16 displayed on the drug abuse test strip 10, the respective pixel positions of the scan line L—L corresponding to each of the color lines 11 through 16 of the drug abuse test strip 10 are assigned. Thereby, the response of each probe zone of the drug abuse test strip 10 to the sample fluid is determined in accordance with the respective pixel value corresponding to the probe zone. The concentration of the detected drug of abuse present in the sample fluid also can be obtained based on the response thereof.

The present method can be automatically performed by an application installed in a computer associated with an image capturing device. The present method is suitable to be used as means to accurately and rapidly detect or identify the presence or absence of drugs of abuse in the sample fluid. And, the present method does not need an expensive equipment and a sophisticated personnel to perform. Thus, the present invention provides an extremely important advance in the drug abuse detection technology. Thousands of tests will no longer have to be conducted using the more sophisticated TLC, EMIT, RIA and GLC procedures.

The embodiments are only used to illustrate the present invention, not intended to limit the scope thereof. Many modifications of the embodiments can be made without departing from the spirit of the present invention.

What is claimed is:

1. A method for detecting a response for a probe zone on a test strip, comprising:
    providing a test strip having a light color base and a color pattern displayed thereon, said color pattern occurring in response to a tested solution contacting with said test strip and including a plurality of color lines displayed in sequence from a first portion of said test strip to a second portion thereof, the site of a said color line representing a probe zone of said test strip;
    capturing an image of said test strip;
    selecting at least one scan line from the image, said scan line being substantially perpendicular to the image of said color lines;
    setting a pixel position of said scan line having a minimum pixel value corresponding to a first edge of said test strip; and
    assigning respective pixel positions of said scan line corresponding to said color lines of said test strip by using said pixel position with the minimum pixel value as a reference and in accordance with the sequence of said color lines displayed on said test strip, thereby a response of a probe zone of said test strip related to a respective pixel value of one said pixel position corresponding to one said color line is obtained.

2. The method of claim 1, wherein the pixel position of said scan line having a minimum red pixel value is set to correspond to the image of the first edge of said test strip.

3. The method of claim 1, wherein the pixel position of said scan line having a minimum average pixel value formed of red, green, blue pixel values is set to correspond to the image of the first edge of said test strip.

4. The method of claim 1, wherein said test strip has a white base.

5. The method of claim 1, wherein said test strip is a kind of drug abuse test paper having a plurality of probe zones, wherein one probe zone has a color change in response to said tested solution and one or more other probe zones have a color change in response to a drug of abuse in said tested solution.

6. The method of claim 5, wherein said tested solution includes a biological fluid collected from a subject.

7. The method of claim 6, wherein said biological fluid includes a urine specimen fluid.

8. The method of claim 1, wherein the image of said test strip is captured by a scanner associated with a charge-coupled device.

9. A method for selecting a reference to identify an image of a response of a probe zone on a test strip, comprising:
    providing a test strip having a color pattern displayed thereon, said color pattern occurring in response to a tested solution contacting with said test strip and including a plurality of color lines displayed in sequence from a first portion of said test strip to a second portion thereof, the site of a said color line representing a probe zone of said test strip;
    capturing an image of said test strip;
    selecting at least one scan line from the image, said scan line being perpendicular to the image of said color lines; and
    setting a pixel position of said scan line having a minimum pixel value corresponding to the image of a first edge of said test strip and using said pixel position corresponding to the first edge of said test strip as a reference to identify respective pixel positions of said color lines of said test strip on said scan line so as to identify the positions thereof on the image.

10. The method of claim 9, wherein the pixel position of said scan line having a minimum red pixel value is set to correspond to the image of the first edge of said test strip.

11. The method of claim 9, wherein the pixel position of said scan line having a minimum average pixel value formed of red, green, blue pixel values is set to correspond to the image of the first edge of said test strip.

12. The method of claim 9, wherein said test strip has a white base.

13. The method of claim 9, wherein said test strip is a kind of drug abuse test paper having a plurality of probe zones, wherein one probe zone has a color change in response to said tested solution and one or more other probe zones have a color change in response to a drug of abuse in said tested solution.

14. The method of claim 13, wherein said tested solution includes a biological fluid collected from a subject.

15. The method of claim 14, wherein said biological fluid includes a urine specimen fluid.

16. The method of claim 9, wherein the image of said test strip is captured by a scanner associated with a charge-coupled device.

17. A method for detecting a response for a probe zone on a test strip, comprising:
providing a test strip having one or more color lines, wherein a said color line represents a probe zone of said test strip;
capturing an image of said test strip;
selecting at least one scan line from the image, said scan line being substantially perpendicular to said one or more color lines;
setting a pixel position of said scan line having a minimum pixel value corresponding to a first portion of said test strip; and
assigning respective pixel positions of said scan line corresponding to said one or more color lines by using said pixel position with the minimum pixel value as a reference, thereby a response of said probe zone related to a pixel value of one said pixel position corresponding to at least one said color line is obtained.

18. The method of claim 17 wherein said test strip comprises two or more color lines, wherein one said color line has a color change in response to said tested solution and the other said color lines have a color change in response to one or more drugs of abuse in said tested solution.

19. The method of claim 18 wherein each of said other said color lines have a color change in response to a different drug of abuse in said tested solution.

20. The method of claim 17 wherein said respective pixel positions corresponding to said one or more color lines are assigned by sequential positions of said one or more color lines.

21. The method of claim 17, wherein the pixel position of said scan line having a minimum red pixel value is set to correspond to the image of the first portion of said test strip.

22. The method of claim 17, wherein the pixel position of said scan line having a minimum average pixel value formed of red, green, blue pixel values is set to correspond to the first portion of said test strip.

23. The method of claim 17, wherein said test strip has a light color base.

24. The method of claim 17 wherein said test strip has a white color base.

25. The method of claim 17 wherein said test strip has a plurality of color lines.

26. The method of claim 25 wherein said plurality of color lines are arranged substantially parallel to one another.

27. The method of claim 17 wherein said minimum pixel value corresponds to a first edge of said test strip.

* * * * *

UNITED STATES PATENT AND TRADEMARK OFFICE
CERTIFICATE OF CORRECTION

| | | |
|---|---|---|
| PATENT NO. | : 7,197,169 B2 | Page 1 of 1 |
| APPLICATION NO. | : 10/334798 | |
| DATED | : March 27, 2007 | |
| INVENTOR(S) | : Wang | |

It is certified that error appears in the above-identified patent and that said Letters Patent is hereby corrected as shown below:

On the title page item (76), please replace "Ksiao-Kang" with --Hsiao-Kang--.

Signed and Sealed this

Sixth Day of July, 2010

David J. Kappos
*Director of the United States Patent and Trademark Office*